(12) United States Patent
Feng et al.

(10) Patent No.: US 9,642,741 B2
(45) Date of Patent: May 9, 2017

(54) SURGICAL COOLING DEVICE

(76) Inventors: Yusheng Feng, Austin, TX (US); Dipen J. Parekh, San Antonio, TX (US); Richard Dashan Canty, Austin, TX (US); Luis Alberto Davila, Eagle Pass, TX (US); Justin Alexander Long, San Antonio, TX (US)

( * ) Notice: Subject to any disclaimer, the term of this patent is extended or adjusted under 35 U.S.C. 154(b) by 990 days.

(21) Appl. No.: 13/811,834

(22) PCT Filed: Jul. 25, 2011

(86) PCT No.: PCT/US2011/045261
§ 371 (c)(1),
(2), (4) Date: Jul. 9, 2013

(87) PCT Pub. No.: WO2012/012807
PCT Pub. Date: Jan. 26, 2012

(65) Prior Publication Data
US 2013/0296982 A1  Nov. 7, 2013

Related U.S. Application Data

(60) Provisional application No. 61/367,252, filed on Jul. 23, 2010.

(51) Int. Cl.
*A61B 18/02* (2006.01)
*A61F 7/12* (2006.01)
*A61F 7/00* (2006.01)

(52) U.S. Cl.
CPC ........ *A61F 7/12* (2013.01); *A61F 2007/0056* (2013.01); *A61F 2007/0087* (2013.01); *A61F 2007/126* (2013.01)

(58) Field of Classification Search
CPC ...... A61F 7/12; A61F 7/123; A61F 2007/101; A61F 2007/0054; A61F 2007/0056; A61F 2007/126
USPC .................................................. 607/105, 113
See application file for complete search history.

(56) References Cited

U.S. PATENT DOCUMENTS

| | | | | |
|---|---|---|---|---|
| 4,154,245 A | * | 5/1979 | Daily | A61F 7/10 607/105 |
| 5,014,695 A | * | 5/1991 | Benak | A61F 7/12 165/46 |
| 5,150,706 A | * | 9/1992 | Cox | A61F 7/10 128/897 |
| 2002/0068902 A1 | * | 6/2002 | Larnard | A61F 7/12 604/113 |

(Continued)

*Primary Examiner* — Jocelyn D Ram
(74) *Attorney, Agent, or Firm* — Jackson Walker LLP

(57) ABSTRACT

Surgical cooling may be implemented by various systems, processes, and techniques. In certain implementations, a surgical cooling device includes a shaft, a cooling assembly, and a mechanical control system. The shaft includes a pair of axial cooling channels extending through its interior. The cooling assembly includes a pair of arms pivotally attached to the shaft and a foldable thermal exchanger coupled to the pair of arms and fluidly coupled to the pair of axial cooling channels. The mechanical control system is adapted to unfold the cooling assembly from a closed position to an open position to allow a coolant to flow through a first of the pair of axial cooling channels, through one or more thermal exchange channels, and out a second of the pair of cooling channels.

21 Claims, 16 Drawing Sheets

(56) References Cited

U.S. PATENT DOCUMENTS

| | | | | |
|---|---|---|---|---|
| 2002/0156470 | A1* | 10/2002 | Shadduck | A61B 18/1485 |
| | | | | 606/41 |
| 2004/0034321 | A1* | 2/2004 | Larnard | A61F 7/123 |
| | | | | 604/113 |
| 2004/0049154 | A1* | 3/2004 | Larnard | A61F 7/123 |
| | | | | 604/103.07 |
| 2004/0267338 | A1* | 12/2004 | Harrison | A61F 7/12 |
| | | | | 607/105 |
| 2008/0008987 | A1* | 1/2008 | Bianco | A01N 1/02 |
| | | | | 435/1.2 |
| 2010/0292764 | A1* | 11/2010 | Soomro | A61F 7/12 |
| | | | | 607/105 |
| 2012/0203312 | A1* | 8/2012 | Batzer | A61F 7/02 |
| | | | | 607/105 |

* cited by examiner

US 9,642,741 B2

SURGICAL COOLING DEVICE

RELATED APPLICATIONS

This application is a 371 of PCT Application No. PCT/US11/45261, entitled "Surgical Cooling Device" and filed on Jul. 25, 2011, which claims priority to U.S. Provisional Application No. 61/367,252, entitled "Surgical Cooling Device" and filed on Jul. 23, 2010. These applications are herein incorporated by reference.

BACKGROUND

This invention relates to the field of medicine and more particularly to a surgical cooling device. The present invention is useful for cooling organs attendant to surgery. For example, in partial nephrectomies, the kidney is often cooled prior to performing the surgery. This specification describes a novel surgical cooling device useful in surgeries where organ cooling is desired. It may be applied in any setting by any approach (open, laparoscopic, robotic and/or any minimally invasive approach) on any organ where surface hypothermia is desired.

SUMMARY OF THE INVENTION

The present invention is a surgical cooling device for cooling organs attendant to surgery. When the surgical cooling device is in use, a coolant circulates inside the device to cool the organ.

An embodiment of the present surgical cooling device comprises a body having a handle and a shaft having a pair of axial cooling channels extending through the interior of the shaft; a cooling assembly comprising a pair of arms pivotally attached to the shaft and a foldable thermal exchanger mounted on the pair of arms and fluidly coupled to the pair of axial cooling channels, the thermal exchanger comprising an inlet port, an outlet port, and one or more exchange channels fluidly connecting the inlet port to the outlet port; and a mechanical control system for opening and closing the cooling assembly, the mechanical control system comprising a rotatable knob with a male threaded end, a plunger with a female threaded opening and an opening adapted to receive a rod, the rod engaging the plunger and a pair of wing connectors, the wing connectors attached to the rod and the pair of arms; wherein the cooling assembly unfolds from a closed position to an open position and folds from the open position to the closed position in response to rotation of the knob; and wherein a coolant flows through a first of the pair of axial cooling channels, through the one or more exchange channels, and out a second of the pair of cooling channels.

An alternative embodiment of the present surgical cooling device comprises (A) a body including a handle, a shaft adjacent to the handle, a pair of shoulders adjacent to the shaft, and a pair of axial cooling channels extending through the interiors of the handle and the shaft, each of the pair of axial cooling channels having at least one inflow and one outflow port; and (B) a cooling assembly including a pair of arms pivotally attached to the pair of shoulders, a pair of fasteners attaching the pair of arms to the pair of shoulders, and a foldable thermal exchanger mounted on the pair of arms and engaging the pair of axial cooling channels; the thermal exchanger comprising an inlet port, an outlet port, one or more exchange channels fluidly connecting the inlet port to the outlet port, and a pair of sleeves at two edges of the thermal exchanger adapted to slip onto the pair of arms; wherein the cooling assembly unfolds from a closed position to an open position and folds from the open position to the closed position; and wherein a cooling media flows into a first of the pair of cooling channels, through the one or more exchange channels, and out a second of the pair of cooling channels.

A surgical cooling device will now be described with more particular reference to the attached drawings.

DETAILED DESCRIPTION OF THE INVENTION

Figure 1:
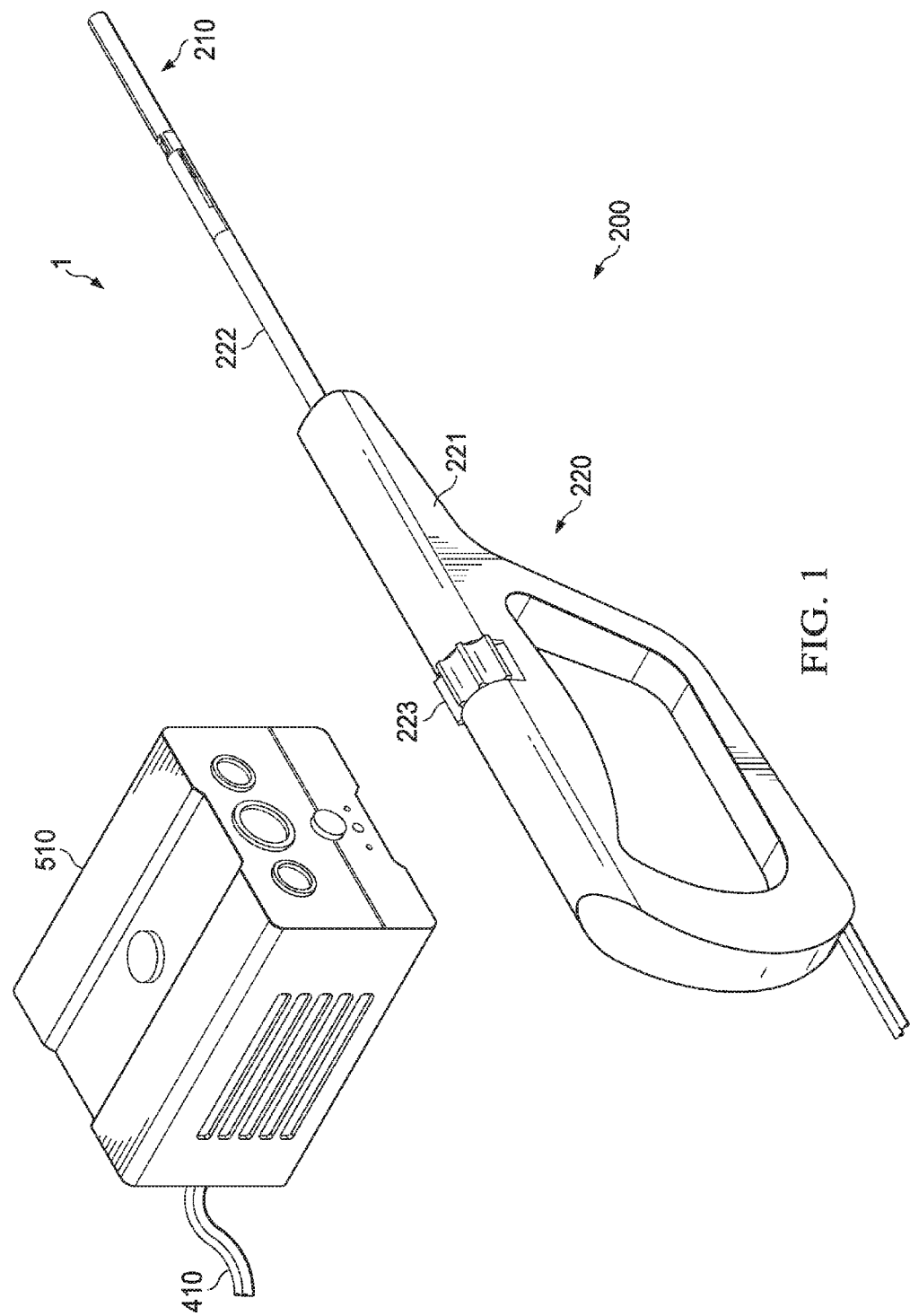
FIG. 1 is a perspective view of a surgical cooling system with a surgical cooling device.

FIG. 1 shows a surgical cooling system 1 comprising one or more surgical cooling devices 200, a chiller/pump system 510, and one or more pairs of hoses or tubes 410. Each pair of tubes 410 comprises an inlet tube for conveying coolant from the chiller/pump system 510 to a surgical cooling device 200 and an outlet tube for conveying coolant from the surgical cooling device 200 to the chiller/pump system 510. Each tubing pair 410 fluidly connects one cooling device 200 to the chiller/pump system 510. The one or more pairs of tubes 410 may be detachably engaged to the one or more cooling devices 200 or the chiller/pump system 510.

The surgical cooling system is a closed, self-contained system, with coolant circulating from the chiller/pump system 510, through an inlet tube of a tubing pair 410, through a surgical cooling device 200, through an outlet tube of a tubing pair 410, and back into chiller/pump system 510. The chiller/pump system 510 circulates chilled fluid or other coolant, either continuously or in an intermittent manner, for cooling an organ to a desired temperature. Off-the-shelf equipment may be used for the chiller/pump system 510, such as Tek-Temp Instruments, Inc.'s LK-10 Light Capacity Chiller. The coolant flow rate and type of coolant may be varied according to the cooling needs of the specific surgery.

Figure 2:
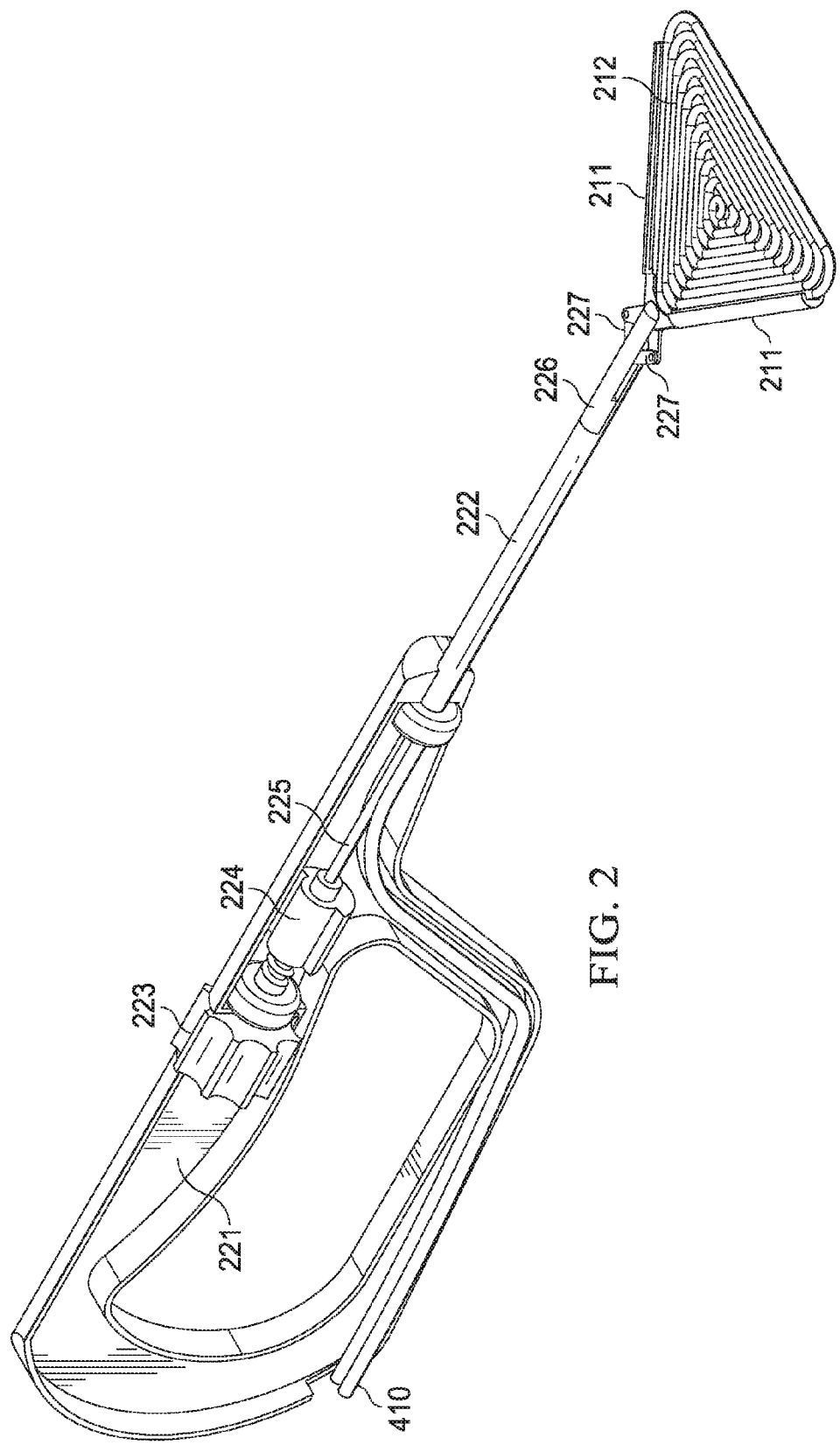
FIG. 2 is a cut-away perspective view of a surgical cooling device with the cooling assembly in an open position.
Figure 3:
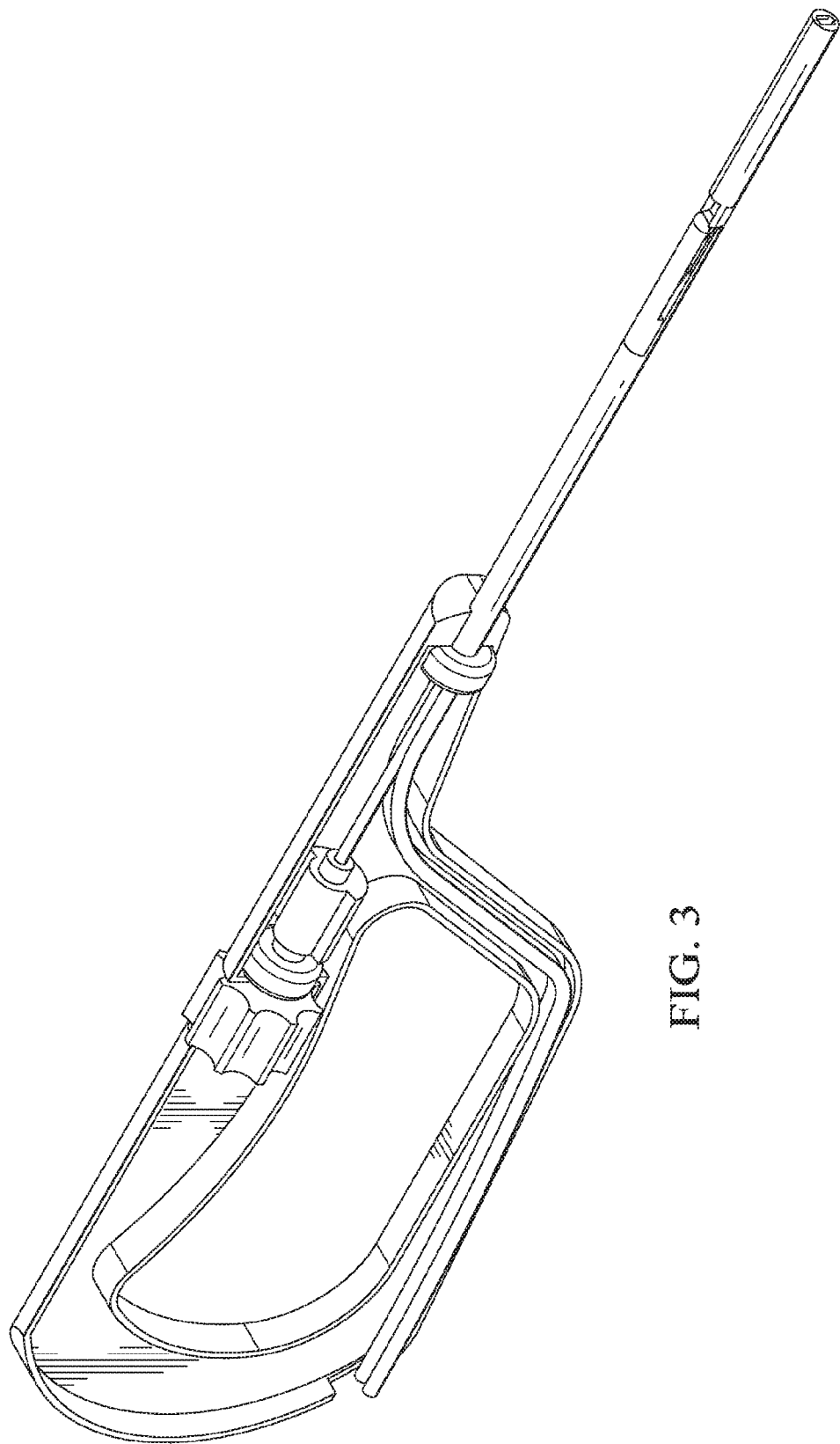
FIG. 3 is a cut-away perspective view of a surgical cooling device with the cooling assembly in a closed position.
Figure 4:
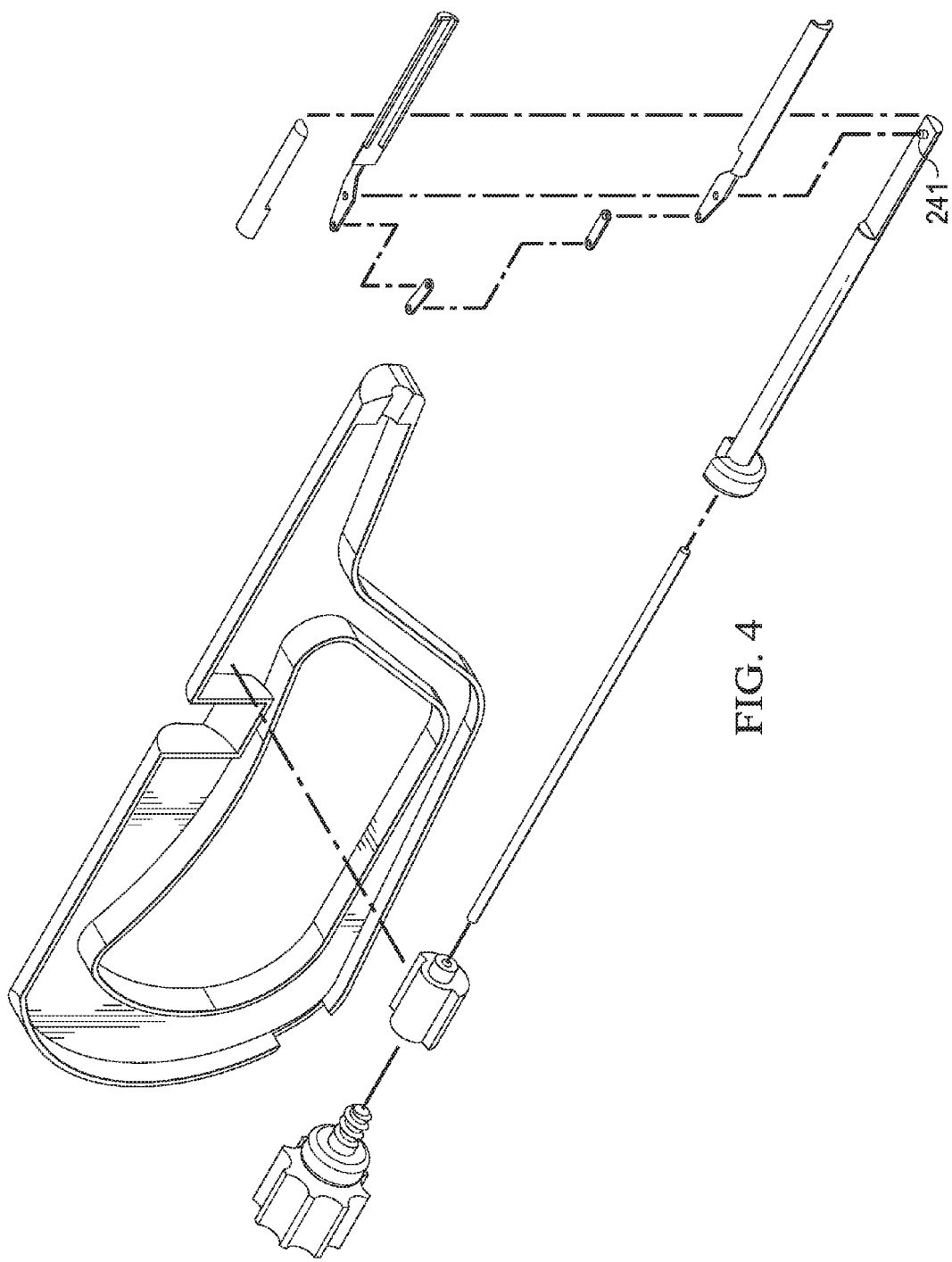
FIG. 4 is an exploded view of a surgical cooling device (thermal exchanger not shown).
Figure 5:
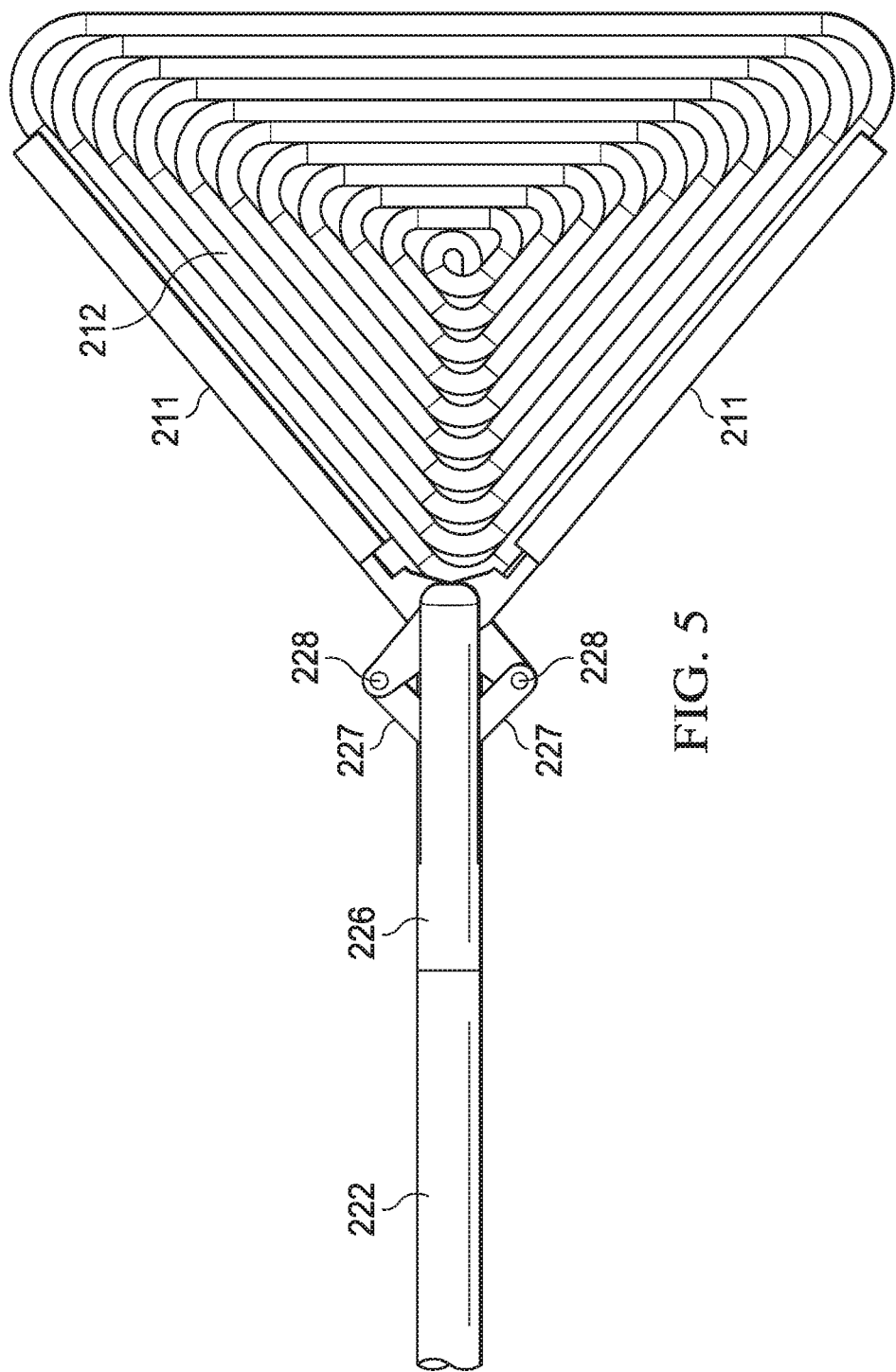
FIG. 5 is a top view of a cooling assembly in an open position.
Figure 6:
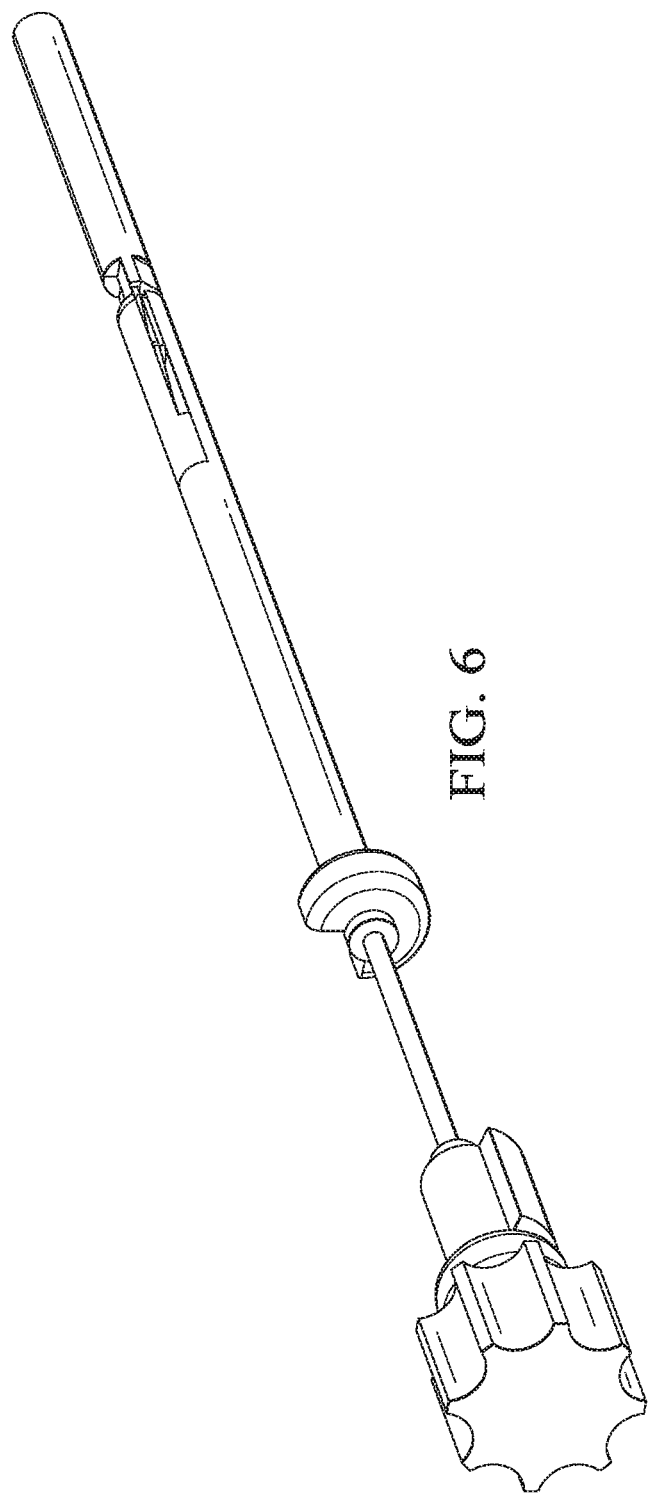
FIG. 6 is a perspective view of a surgical cooling device (handle assembly not shown) with the cooling assembly in a closed position.
Figure 7:
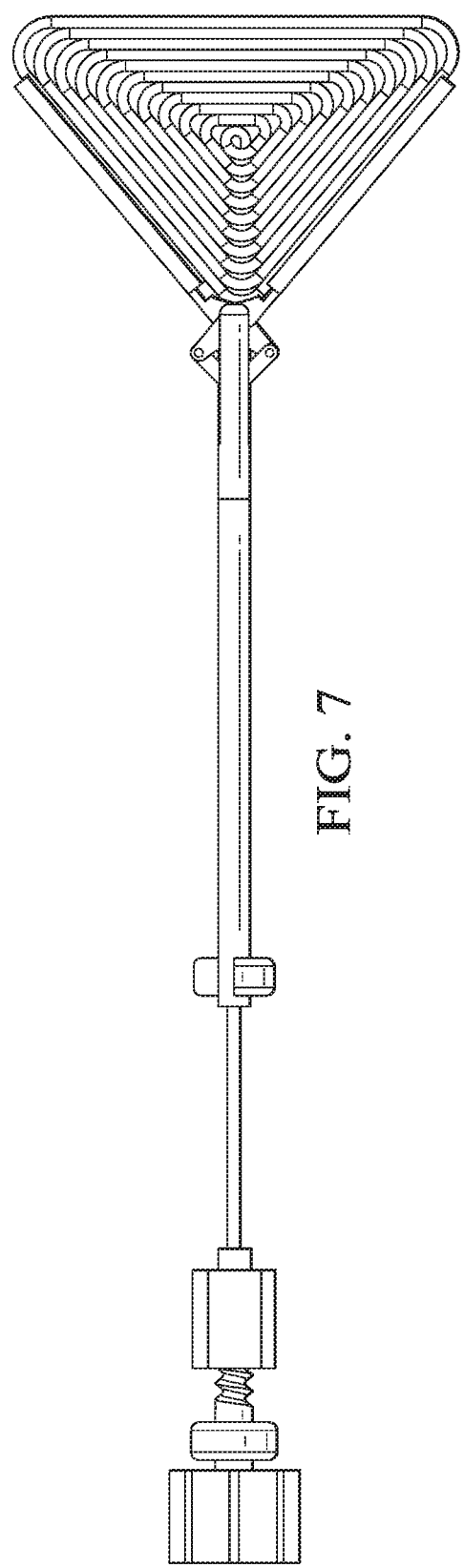
FIG. 7 is a top view of a surgical cooling device (handle assembly not shown) with the cooling assembly in an open position.

As shown in FIG. 1, the surgical cooling device 200 may comprise a body 220 and a cooling assembly 210. Body 220 may include a handle assembly 221, a shaft 222, and a knob 223, all of which may be constructed of stainless steel, durable plastic, or other materials known in the art. Referring to FIG. 2, the cooling assembly 210 may comprise a pair of arms 211 and a thermal exchanger 212. The total length of the surgical cooling device 200 may be about 300 millimeters (mm), but the total length may be varied as needed for placement of the cooling assembly 210 on the target organ. The surgical cooling device 200 may be capable of being deployed laparoscopically or in open surgeries. For example, the surgical cooling device 200 may be inserted into a trocar during use, so the diameter of shaft 222 and cooling assembly 210 (in the closed position) may be 12 mm or sized as needed to enter standard trocars.

Referring to FIG. 2, the cooling assembly 210 comprises a pair of arms 211 and a thermal exchanger 212. The thermal exchanger 212 may be connected to the pair of arms 211. The design and properties of thermal exchanger 212 may be similar to the design and properties of thermal exchanger 112, described in further detail below. In particular, the thermal exchanger 212 may be formed of foldable plastic containing a pattern of channels. The pair of arms 211 may be pivotally attached to the shaft 222 and will open into a generally V-shaped cooling surface. The pair of arms 211 may be mounted on an internal protrusion 241 in shaft 222, with one arm mounted directly above the other, or mounted with a pin or fastener. Each arm of the pair of arms 211 may be about 150 millimeters in length. However, the pair of arms 211 need not be identical in length and may be sized as needed for the procedure. FIG. 2 shows the pair of arms 211 in an open position. In the open position, the angle of separation between the pair of arms 211 may be about 90 degrees; however, this angle may be more or less as appropriate for the specific cooling application. FIG. 1 shows the pair of arms 211 in a closed position, wherein the pair of arms 211 are approximately parallel. The pair of arms 211 may open either symmetrically or asymmetrically about the axis of body 220. The pair of arms 211 may be made of the same material as body 220 or of a different suitable material.

Shaft 222 contains a pair of axial cooling channels. The cooling channels may have cross-sections that are circular in shape, preferably about 5 to 6 mm in diameter. Although each of the cooling channels preferably possesses the same shape and cross-sectional area, the cooling channels may possess dissimilar shapes or cross-sectional areas. The axial cooling channels convey the coolant between the tubing pair 410 and the cooling assembly 210. The thermal exchanger 212 is fluidly coupled to the pair of axial cooling channels within shaft 222.

The cooling device 200 further comprises a plunger 224, a rod 225, a shaft cover 226, and a pair of arm connectors 227. The knob 223 has a male-threaded section that engages a female-threaded opening within plunger 224. Knob 223 additionally comprises a rotation plate, which holds knob 223 in its axial position within the handle assembly 221 while allowing the knob 223 to rotate. The plunger of 224 moves axially in response to the rotation of knob 223. One end of the rod 225 is connected to the plunger 224, typically in a small opening opposite the threaded female opening of the plunger 224. The opposite end of rod 225 connects to the pair of arm connectors 227, typically using a pin or other fastener. The rod 225 passes through an axial rod channel in the shaft 222. The shaft 222 contains a locking plate having a 90 degree cut-out, which holds the shaft 222 in its axial position within the handle assembly 221 and prevents rotation of the shaft 222. One end of each of the pair of arm connectors 227 is connected to the rod 225 and the opposite end is connected to one of the arms 221, typically using a pin or other fastener. The shaft cover 226 is attached to the shaft 222. FIG. 3, FIG. 4, FIG. 5, FIG. 6, and FIG. 7 show further aspects of surgical cooling device 200. Surgical cooling device 200 may be used in a manner similar to the use of surgical cooling device 100, as described below.

Figure 8:
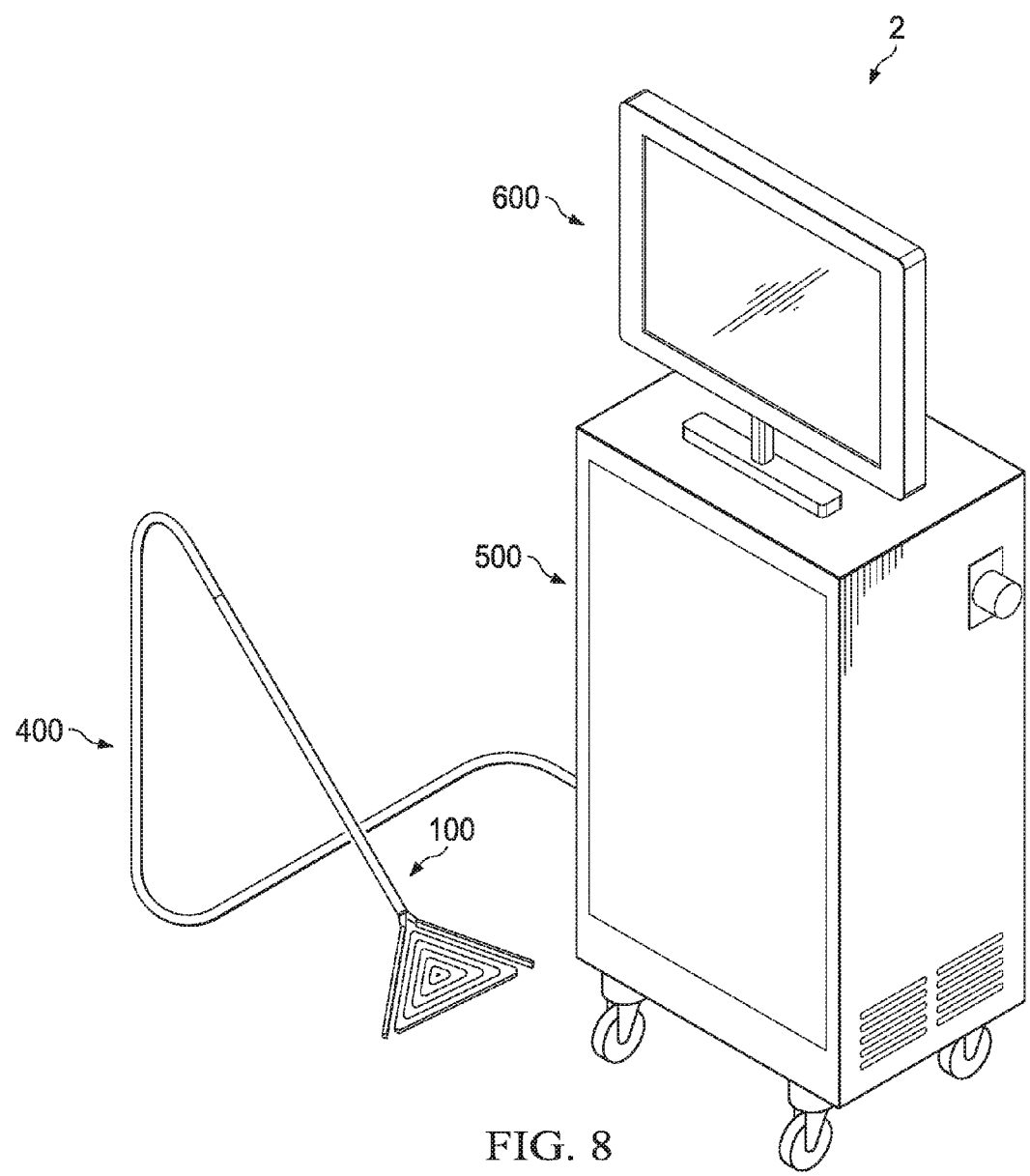
FIG. 8 is a perspective view of a surgical cooling system with an alternative embodiment of a surgical cooling device.

FIG. 8 shows a surgical cooling device 100 in a surgical cooling system 2. The surgical cooling system comprises one or more surgical cooling devices 100, a chiller/pump system 500, a graphical user interface 600, and one or more hoses or tubes 400. The one or more hoses or tubes 400 are coupled to the chiller/pump system 500 and detachably engage the one or more surgical cooling device 100. The chiller/pump system 500 maintains coolant at the desired temperature and continuously pumps coolant into the one or more surgical cooling devices 100. The coolant flow rate and coolant may be varied according to the specific surgery. The surgical cooling system is a closed, self-contained system with coolant circulating out of the chiller/pump system 500, through the one or more hoses or tubes 400, through the one or more surgical cooling devices 100, back through the one or more hoses or tubes 400, and into chiller/pump system 500. The surgical cooling device 100 is capable of being deployed laparoscopically or in open surgeries, and may be reusable or disposed after a single-use.

Figure 9:
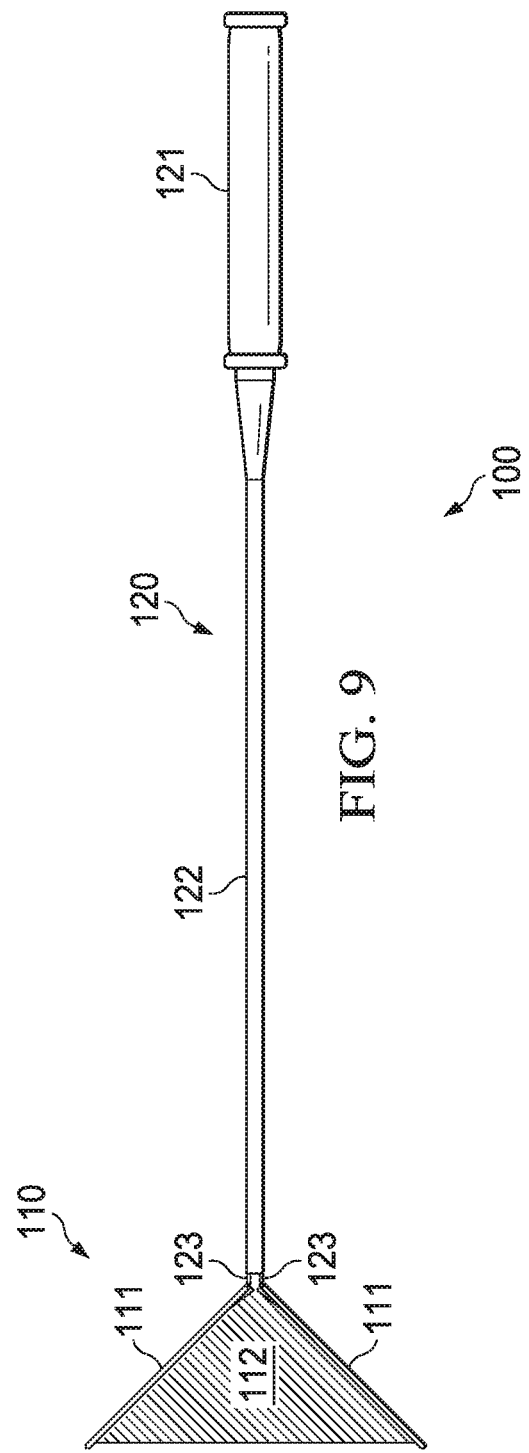
FIG. 9 is a top view of an alternative surgical cooling device.

FIG. 9 discloses an embodiment of a surgical cooling device 100. The surgical cooling device 100 comprises a cooling assembly 110 and a body 120. Surgical cooling device 100 is Y-shaped when in the open position as shown in FIG. 9. Body 120 may include a handle 121, a shaft 122, and a pair of shoulders 123, all of which are preferably made of plastic. Handle 121, shaft 122, and pair of shoulders 123 may be integrally manufactured, welded together, or coupled with fasteners such as screws. The total length of the surgical cooling device 100 is preferably about 300 millimeters (mm). However, the total length of surgical cooling device 100 may be optimized to allow precise extension to the target organ based on the application.

Figure 10:
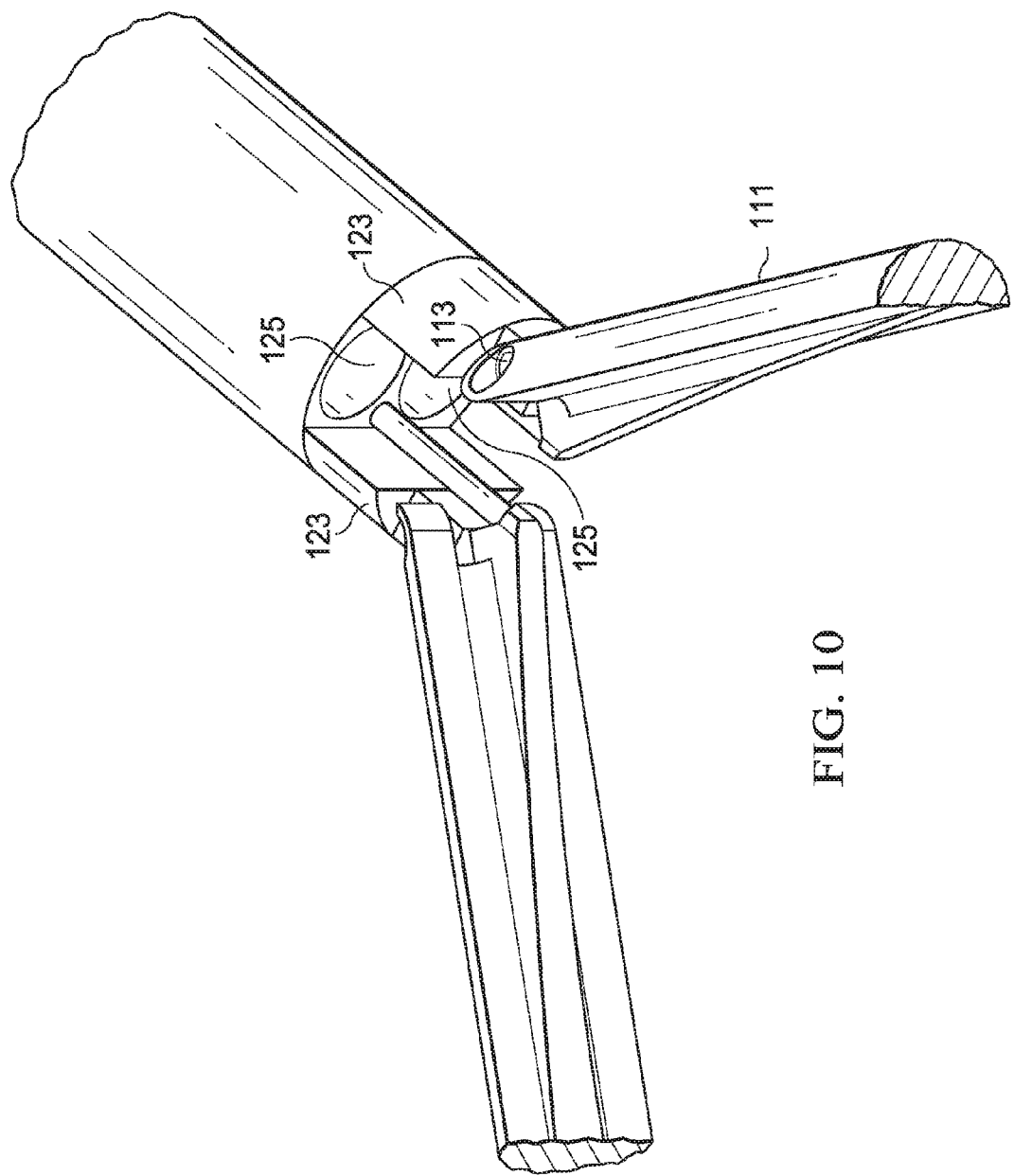
FIG. 10 is an enlarged perspective view of an alternative embodiment of a surgical cooling device (thermal exchanger not shown).

When in use, the surgical cooling device 100 is capable of being inserted into and engaging a 12 mm diameter trocar. Accordingly, the diameter of body 120 is preferably at least 12 mm. Referring now to FIG. 10, body 120 further comprises typically a pair of axial cooling channels 125 running through handle 121 and shaft 122. Each of the pair of cooling channels 125 has at least one inflow and one outflow port. The cooling channels 125 may have cross-sections that are circular in shape, preferably about 5.5 mm in diameter. Although each of the cooling channels 125 preferably possesses the same shape and cross-sectional area, the cooling channels 125 may possess dissimilar shapes or cross-sectional areas.

Figure 11:
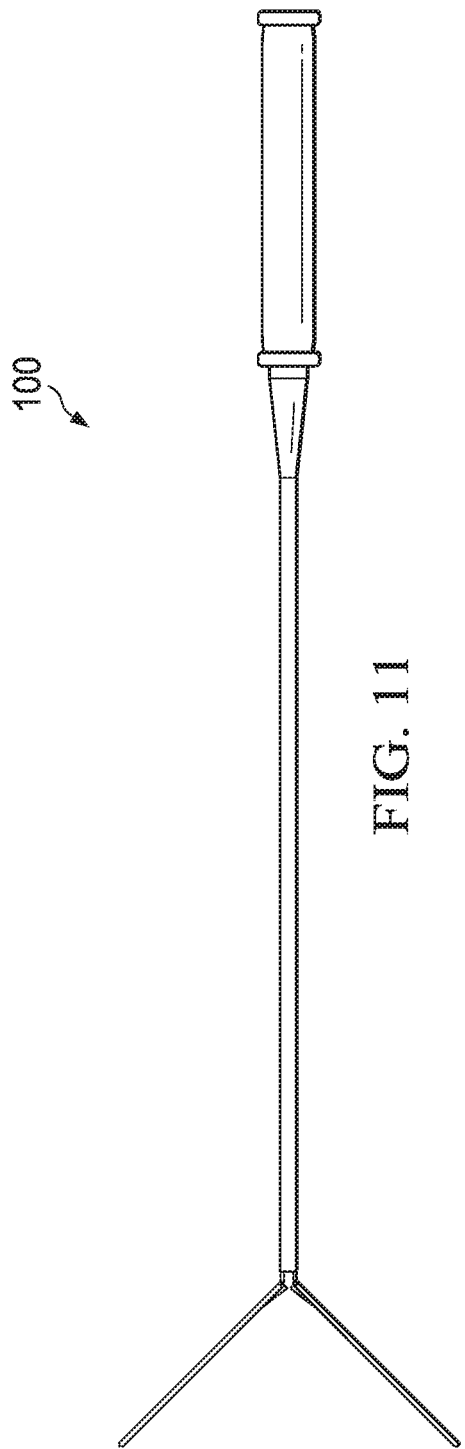
FIG. 11 is a top view of an alternative embodiment of a surgical cooling device with the arms in the open position (thermal exchanger not shown).
Figure 12:
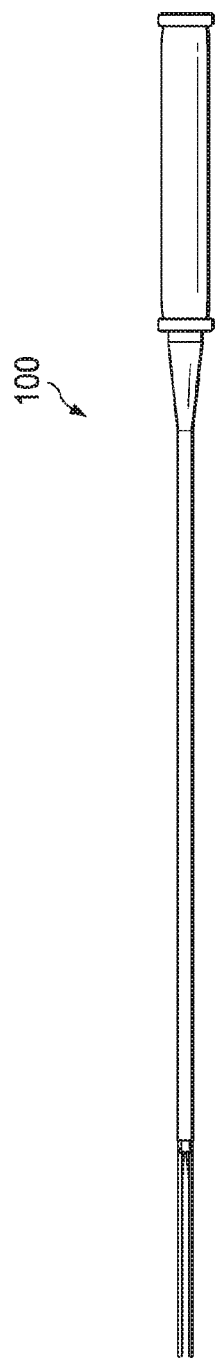
FIG. 12 is a top view of an alternative embodiment of a surgical cooling device with the arms in the closed position (thermal exchanger not shown).

Referring back to FIG. 9, the cooling assembly 110 comprises a pair of arms 111 and a thermal exchanger 112. The pair of arms 111 may be pivotally attached to the pair of shoulders 123. Fasteners 113, such as locking pins or screws, mount the pair of arms 111 to the pair of shoulders 123. Each arm of the pair of arms 111 is preferably about 150 millimeters in length. However, the pair of arms 111 need not be identical in length. FIG. 9 and FIG. 11 shows the pair of arms 111 in an open position. In the open position, the angle of separation between the pair of arms 111 in a preferred embodiment is about 90°; however, this angle may be more or less as required for the specific cooling application. FIG. 12 shows the pair of arms 111 in a closed position, wherein the pair of arms 111 are approximately parallel. The pair of arms 111 may open either symmetrically or asymmetrically about the axis of body 120. The pair of arms 111 may be made of the same material as body 120 or of a different suitable material.

Thermal exchanger 112 may be triangular or sectoral in shape and includes an inlet port, an outlet port, one or more exchange channels fluidly connecting the inlet port to the outlet port, and typically a pair of sleeves adapted to slip onto the pair of arms 111 of the cooling assembly 110. The pair of sleeves adapted to slip onto the pair of arms 111 are preferably positioned at or near the edges of thermal exchanger 112. The inlet port and outlet port of thermal exchanger 112 may be permanently or removably secured to or integrated with the cooling channels 125 of the body 120. Alternatively, the inlet port and outlet port may include a fitting or connector adapted to detachably engage the cooling channels 125 of the body 120. Such fittings or connectors may be standard fluid fittings, such as Luer lock fittings, barbed fittings, or proprietary fittings.

The one or more exchange channels of thermal exchanger 112 connect the inlet port to the outlet port, preferably without overlapping sections of exchange channel. For example, a single exchange channel may follow a generally zigzag or serpentine path from the inlet port to the outlet port without overlapping sections. A generally circular flow path may also be created without overlapping sections of channel. Alternatively, one or more sections of the one or more exchange channels may overlap within thermal exchanger 112. The total cross-sectional area of the exchange channels of thermal exchanger 112 is preferably (A) constant along the length of the exchange channels and (B) equal to the cross-sectional area of one of the pair of axial cooling channels 125. As the number of exchange channels increases, the cross-sectional area of each individual exchange channel may be decreased, keeping the total cross-section area of the one or more exchange channels constant.

Cooling assembly 110 provides a flexible surface to facilitate heat transfer from the organ to the coolant. Thermal exchanger 112 typically folds and expands, accordion- or fan- like, as the pair of arms 111 move to the closed and open positions, respectively. Consequently, thermal exchanger 112 should be non-rigid, thermally conductive, and made from sufficiently strong material to withstand the pressure of the coolant circulating through surgical cooling device 100. Generally, thermal exchanger 112 may be constructed of polymer film materials capable of handling the stress and pressure of the circulating coolant. Plastics, such as polyurethane film, are the preferred material for constructing thermal exchanger 112. When polyurethane film is used, the one or more exchange channels of thermal exchanger 112 may be formed by radio-frequency welding two sheets of polyurethane in the desired exchange channel pattern. With respect to radio-frequency welding polyurethane sheets, although thermal exchanger 112 is initially empty, the one or more exchange channels will inflate with coolant as the coolant flows through the surgical cooling device 100. To create a coolant-inflated exchange channel of approximately diameter D, the polyurethane film welds on the empty thermal exchanger 112 should be spaced approximately 1.57 D apart. An array of thermocouples may be embedded in or mounted on thermal exchanger 112 to measure the temperature distribution across all or part of thermal exchanger 112.

When surgical cooling device 100 is used, the pair of arms 111 are first moved to the open position shown in FIG. 11, and cooling assembly 110 is positioned on the organ to be cooled. The cooling assembly 110 may be opened and closed by manually grasping the pair of arms 111 and opening or closing the arms 111. Coolant then flows into a first of the cooling channels 125, through the inlet port of thermal exchanger 112, through the one or more exchange channels of thermal exchanger 112, through the outlet port of thermal exchanger 112, and out a second of the cooling channels 125. Thus, flow through thermal exchanger 112 is unidirectional. As the coolant flows through the one or more exchange channels, it absorbs heat from the organ. The coolant may be a fluid that is safe for use during surgery, such as water, ice slurry, cold air, ideal gas, or a saline solution. The coolant is circulated at a temperature and flow rate such that the organ temperature is able to drop to at least 10 degrees Celcius as the coolant flows through the thermal exchanger 112. To measure the heat transfer, surgical cooling device 100 may include a pair of thermocouples embedded (as by insert molding) in the cooling channels 125 at or near the thermal exchanger 112, preferably with one thermocouple in each cooling channel. The wires for the thermocouples may be routed through the cooling channels 125 or may be embedded in the body 120 of surgical cooling device 100.

Figure 13:
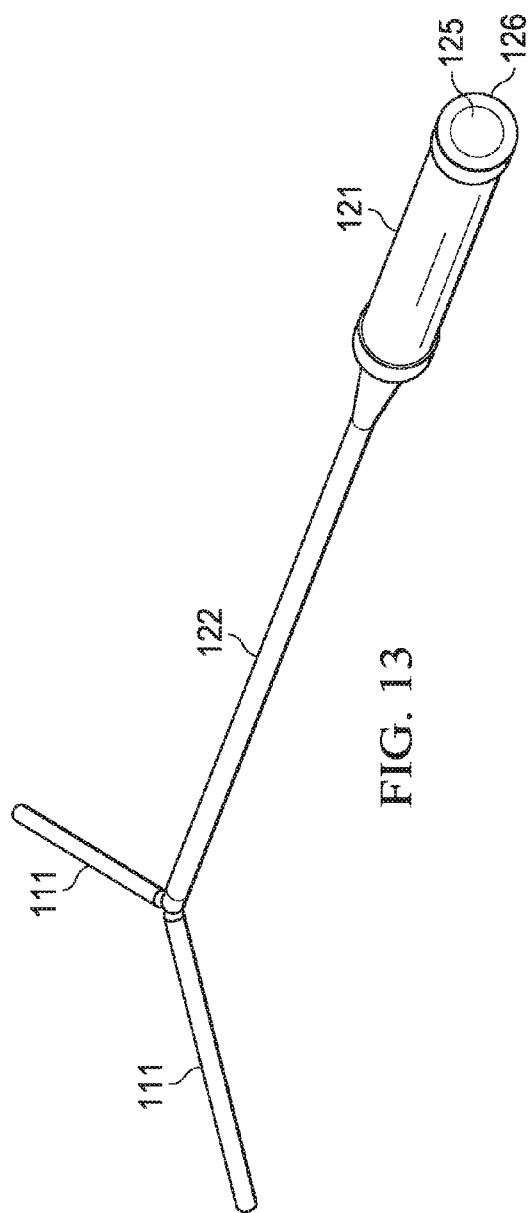
FIG. 13 is a perspective view of an alternative embodiment of a surgical cooling device (thermal exchanger not shown).
Figure 14:
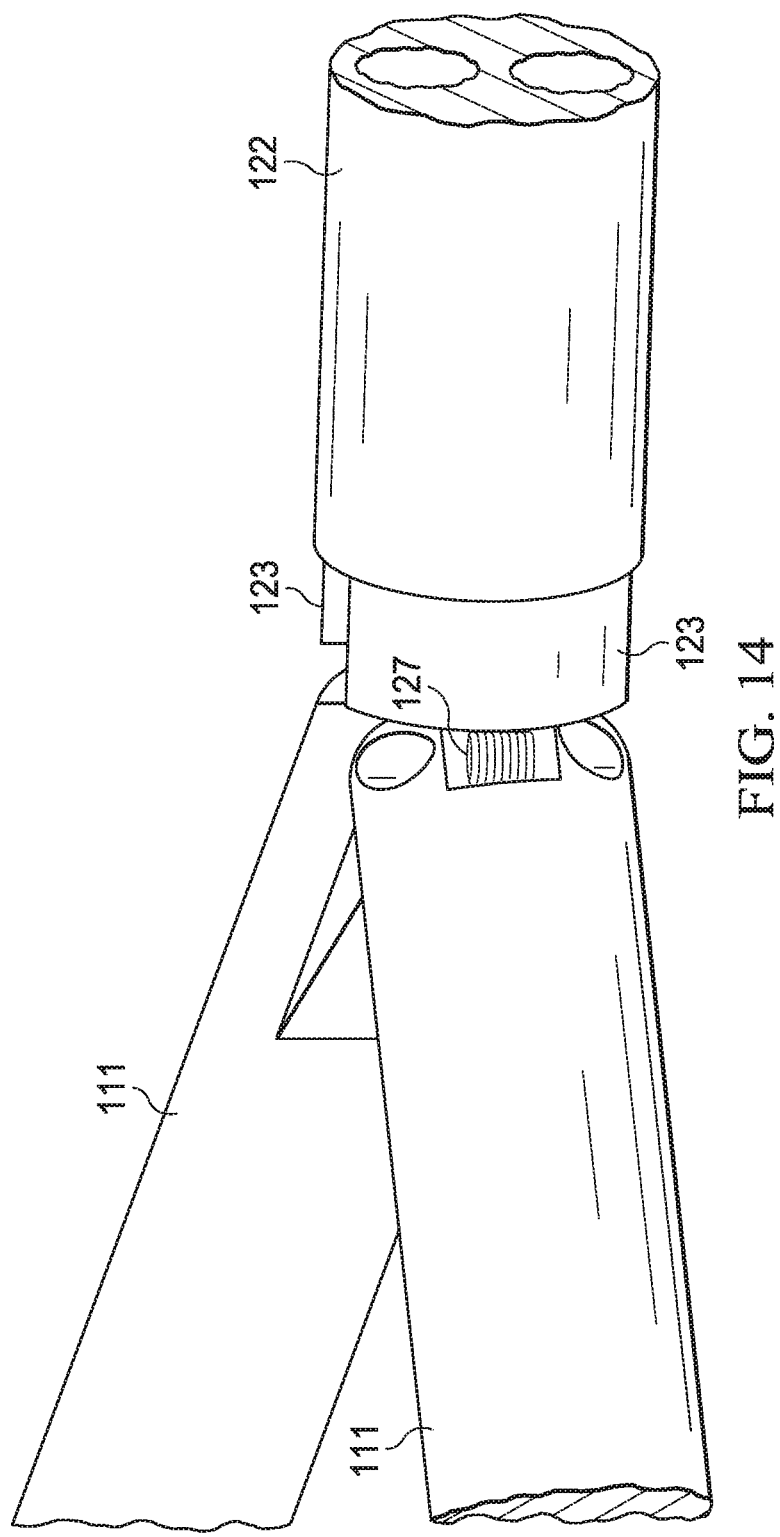
FIG. 14 is an enlarged perspective view of an alternative embodiment of a surgical cooling device (thermal exchanger not shown).

FIG. 13 shows another view of surgical cooling device 100. In surgical cooling device 100, the handle 121 of body 120 includes a rubber grip 126 to provide a better hold. The rubber grip 126 may be smooth or textured. Referring to FIG. 14, surgical cooling device 100 includes a pair of torsional springs 127 at the joint between the pair of shoulders 123 and the pair of arms 111. One purpose of torsional springs 127 is to aid in keeping the pair of arms 111 in the closed position when the surgical cooling device 100 is inserted or retracted. Thus, the pair of torsional springs 127 are oriented so as to exert a force on the pair of arms 111 toward the closed position. The torsional springs 127 are preferably of sufficient strength to force the pair of arms 111 into the closed position when the arms are unrestrained.

Figure 15:
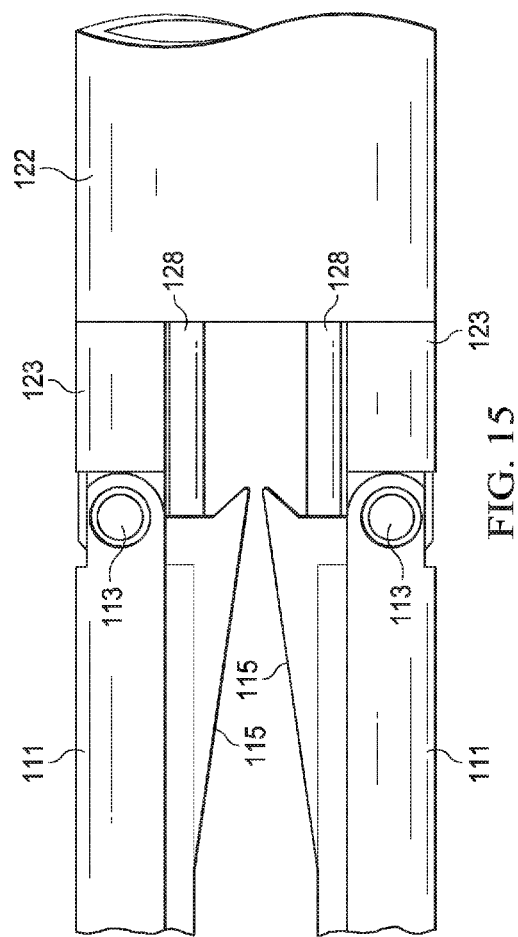
FIG. 15 is an enlarged side view of an alternative embodiment of a surgical cooling device (thermal exchanger not shown).
Figure 16:
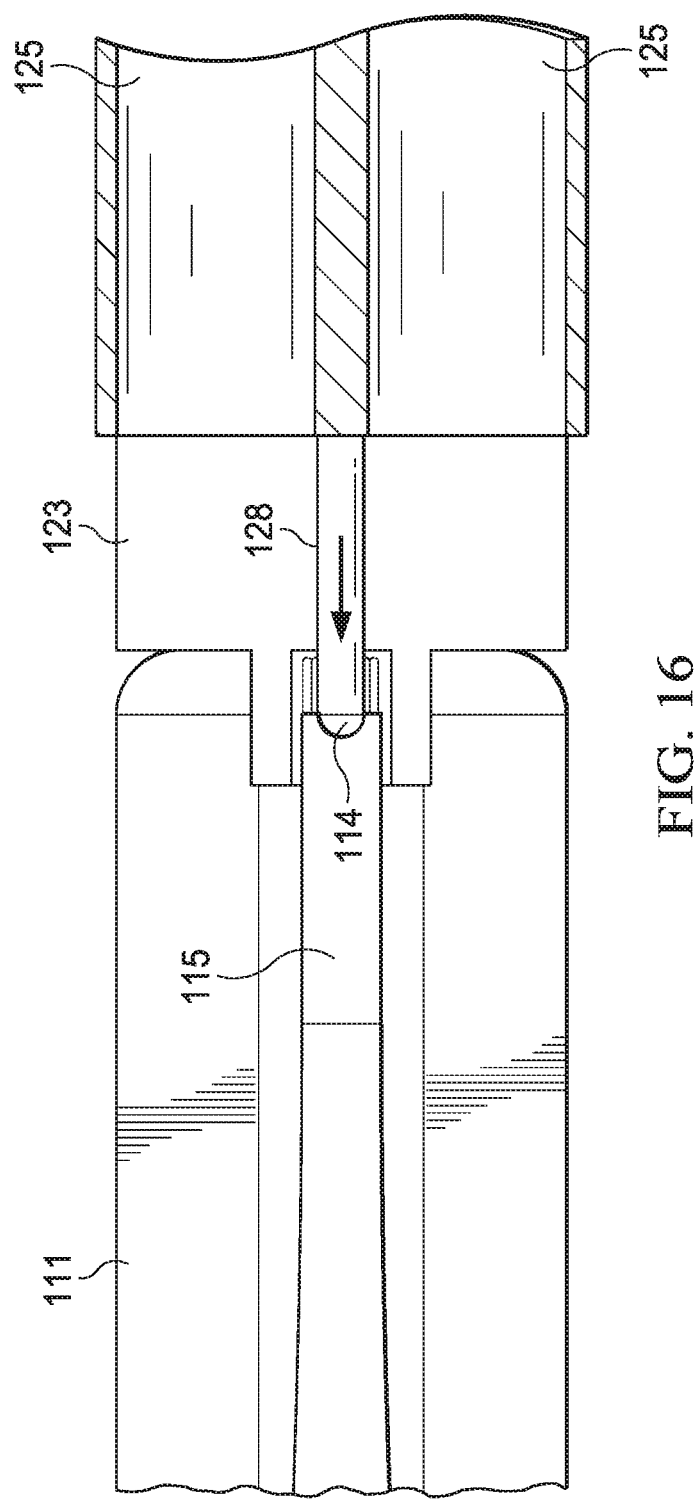
FIG. 16 is an enlarged cross-section view of an alternative embodiment of a surgical cooling device (thermal exchanger not shown).
Figure 17:
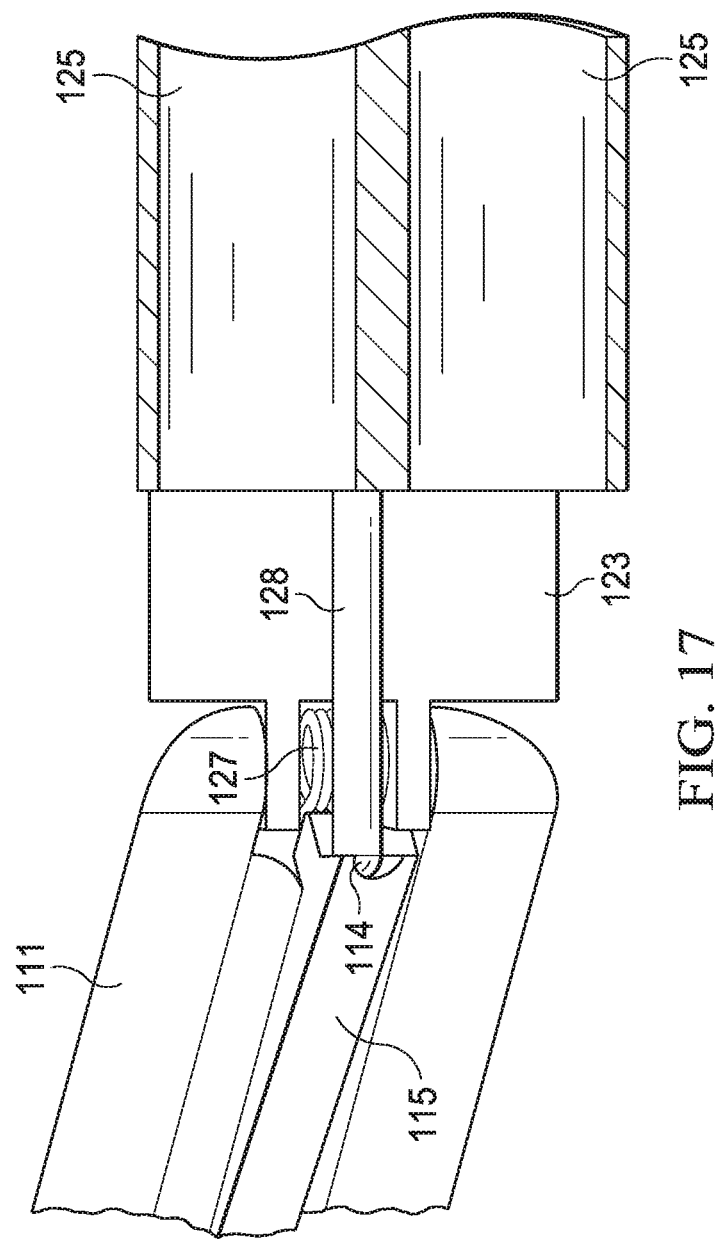
FIG. 17 is an enlarged cross-section view of an alternative embodiment of a surgical cooling device (thermal exchanger not shown).

To facilitate opening the pair of arms 111, surgical cooling device 100 includes an opening mechanism, illustrated in FIG. 15, FIG. 16, and FIG. 17. The opening mechanism comprises a pair of axial rod channels in body 120, a pair of rods 128 positioned inside and slidable within the rod channels, and a control lever attached to the pair of rods 128. Each rod 128 is adapted to engage a hemispherical indentation 114 on a wedge 115 on one of the pair of arms 111. The wedge 115 on each of the pair of arms 111 protrudes inwardly toward the opposite arm. The hemispherical indentation 114 is adapted to receive a rod. FIG. 16 shows the direction the pair of rods 128 move when opening the pair of arms 111. FIG. 17 shows another view of a rod 128 engaging a hemispherical indentation 114. When the pair of arms 111 are in the open position, the arm control mechanism may be locked, for example with a cap and lock system (not shown in the Figures). Rubber grip 126 may be operable to lock the pair of arms 111 in an open position.

While the subject of this specification has been described in connection with one or more exemplary embodiments, it is not intended to limit the claims to the particular forms set forth. On the contrary, the appended claims are intended to cover such alternatives, modifications and equivalents as may be included within their spirit and scope.

What is claimed is:

1. A surgical cooling device comprising:
    a shaft having a pair of axial channels extending through the interior of the shaft;
    a cooling assembly comprising a pair of arms pivotally attached to the shaft and a foldable thermal exchanger coupled to the pair of arms and fluidly coupled to the pair of axial channels, the thermal exchanger comprising an inlet port, an outlet port, and one or more thermal exchange channels fluidly connecting the inlet port to the outlet port; and
    a mechanical control system for activating the pair of arms to unfold the thermal exchanger from a closed position to an open position to allow a coolant to flow through a first of the pair of axial cooling channels, through the one or more exchange channels, and out a second of the pair of axial cooling channels;
    wherein the mechanical control system further comprises a rod and a pair of wing connectors, the wing connectors attached to the rod and the pair of arms, wherein the cooling assembly unfolds from the closed position to the open position and folds from the open position to the closed position in response to activation of the rod.

2. The surgical cooling device of claim 1 wherein the thermal exchanger is formed of polyurethane plastic.

3. The surgical cooling device of claim 1 wherein the mechanical control system also activates the pair of arms to fold the thermal exchanger from the open position to the closed position.

4. The surgical cooling device of claim 1 wherein the mechanical control system further comprises a handle including a rotatable knob with a male threaded end and a plunger with a female threaded opening and an opening adapted to receive the rod.

5. The surgical cooling device of claim 1 further comprising:
    a pair of shoulders adjacent to the shaft; and
    a pair of torsional springs engaging the pair of shoulders and the pair of arms.

6. The surgical cooling device of claim 5 further comprising a handle including a rubber grip and a pair of axial members coupled between the rubber grip and wedges on the arms to activate the arms, wherein the rubber grip is operable to lock the pair of arms in the open position.

7. The surgical cooling device of claim 1 wherein one of the thermal exchange channels has a serpentine shape.

8. The surgical cooling device of claim 1 wherein one of the thermal exchange channels overlaps on itself.

9. The surgical cooling device of claim 1 further comprising a pair of sleeves at two edges of the thermal exchanger, the sleeves adapted to slip onto the pair of arms.

10. The surgical cooling device of claim 1 wherein the device is approximately 12 mm in diameter when in the closed position.

11. A surgical cooling device comprising:
    a shaft having a pair of axial channels extending through the interior of the shaft;
    a cooling assembly comprising a pair of arms pivotally attached to the shaft and a foldable thermal exchanger coupled to the pair of arms and fluidly coupled to the pair of axial channels, the thermal exchanger comprising an inlet port, an outlet port, and one or more thermal exchange channels fluidly connecting the inlet port to the outlet port;
    a mechanical control system for activating the pair of arms to unfold the thermal exchanger from a closed position to an open position to allow a coolant to flow through a first of the pair of axial cooling channels, through the one or more exchange channels, and out a second of the pair of axial cooling channels;
    a pair of shoulders adjacent to the shaft; and
    a pair of torsional springs engaging the pair of shoulders and the pair of arms.

12. The surgical cooling device of claim 11 wherein the thermal exchanger is formed of polyurethane plastic.

13. The surgical cooling device of claim 11 wherein the mechanical control system also activates the pair of arms to fold the thermal exchanger from the open position to the closed position.

14. The surgical cooling device of claim 11 wherein the mechanical control system further comprises a rod and a pair of wing connectors, the wing connectors attached to the rod and the pair of arms, wherein the cooling assembly unfolds from the closed position to the open position and folds from the open position to the closed position in response to activation of the rod.

15. The surgical cooling device of claim 14 wherein the mechanical control system further comprises a handle including a rotatable knob with a male threaded end and a plunger with a female threaded opening and an opening adapted to receive the rod.

16. The surgical cooling device of claim 11 further comprising a handle including a rubber grip and a pair of axial members coupled between the rubber grip and wedges on the arms to activate the arms, wherein the rubber grip is operable to lock the pair of arms in the open position.

17. The surgical cooling device of claim 11 wherein one of the thermal exchange channels has a serpentine shape.

18. The surgical cooling device of claim 11 wherein one of the thermal exchange channels overlaps on itself.

19. The surgical cooling device of claim 11 further comprising a pair of sleeves at two edges of the thermal exchanger, the sleeves adapted to slip onto the pair of arms.

20. The surgical cooling device of claim 11 wherein the device is approximately 12 mm in diameter when in the closed position.

21. A surgical cooling device comprising:
    a body comprising a handle, a shaft adjacent to the handle, a pair of shoulders adjacent to the shaft, and a pair of axial cooling channels extending through the interiors of the handle and the shaft, each of the pair of axial cooling channels having at least one inflow and one outflow port; and
    a cooling assembly comprising a pair of arms pivotally attached to the pair of shoulders, a pair of fasteners attaching the pair of arms to the pair of shoulders, and a foldable thermal exchanger mounted on the pair of arms and engaging the pair of axial cooling channels;
    the thermal exchanger comprising an inlet port, an outlet port, one or more exchange channels fluidly connecting the inlet port to the outlet port, and a pair of sleeves at two edges of the thermal exchanger adapted to slip onto the pair of arms;

wherein the cooling assembly unfolds from a closed position to an open position and folds from the open position to the closed position; and wherein a coolant flows into a first of the pair of cooling channels, through the one or more exchange channels, and out a second of the pair of cooling channels.

* * * * *